US009211420B2

(12) United States Patent
Patel et al.

(10) Patent No.: US 9,211,420 B2
(45) Date of Patent: *Dec. 15, 2015

(54) KIT CONTAINING PHOTOSENSITIZING DYES

(75) Inventors: Madhusudan Patel, Somerset, NJ (US); Rosa Paredes, North Brunswick, NJ (US); Mahmoud Hassan, Somerset, NJ (US); Thomas Boyd, Metuchen, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/518,094

(22) PCT Filed: Dec. 20, 2010

(86) PCT No.: PCT/US2010/061329
§ 371 (c)(1),
(2), (4) Date: Jun. 21, 2012

(87) PCT Pub. No.: WO2011/084746
PCT Pub. Date: Jul. 14, 2011

(65) Prior Publication Data
US 2012/0264078 A1   Oct. 18, 2012

Related U.S. Application Data

(60) Provisional application No. 61/288,360, filed on Dec. 21, 2009.

(51) Int. Cl.
| *A61K 35/74* | (2015.01) |
| *A61K 8/25* | (2006.01) |
| *A61Q 11/00* | (2006.01) |
| *A61N 5/06* | (2006.01) |
| *A61K 8/02* | (2006.01) |
| *A61K 8/35* | (2006.01) |
| *A61K 8/46* | (2006.01) |
| *A61K 8/49* | (2006.01) |
| *A61Q 17/00* | (2006.01) |

(52) U.S. Cl.
CPC ............ *A61N 5/0624* (2013.01); *A61K 8/0208* (2013.01); *A61K 8/35* (2013.01); *A61K 8/466* (2013.01); *A61K 8/494* (2013.01); *A61N 5/0601* (2013.01); *A61N 5/062* (2013.01); *A61N 5/0603* (2013.01); *A61Q 11/00* (2013.01); *A61Q 17/005* (2013.01); *A61K 2800/434* (2013.01); *A61K 2800/81* (2013.01); *A61K 2800/88* (2013.01); *A61N 2005/0606* (2013.01); *A61N 2005/0662* (2013.01)

(58) Field of Classification Search
CPC . A61K 2800/92; A61K 35/74; A61K 6/0058; A61K 8/25; A61Q 11/00; A61Q 17/005
USPC .................. 424/49, 401, 93.4, 9.71
See application file for complete search history.

(56) References Cited

U.S. PATENT DOCUMENTS

| 4,553,936 A | 11/1985 | Wang |
| 4,867,682 A | 9/1989 | Hammesfahr et al. |
| 5,316,473 A | 5/1994 | Hare |
| 5,487,662 A | 1/1996 | Kipke et al. |
| 5,611,793 A | 3/1997 | Wilson et al. |
| 5,776,435 A | 7/1998 | Gaffar et al. |
| 6,162,055 A | 12/2000 | Montgomery et al. |
| 6,337,357 B1 | 1/2002 | Fukunishi et al. |
| 6,343,933 B1 | 2/2002 | Montgomery et al. |
| 6,389,193 B1 | 5/2002 | Kimmel et al. |
| 6,528,555 B1 * | 3/2003 | Nikutowski et al. .......... 523/116 |
| 6,616,447 B1 | 9/2003 | Rizoiu et al. |
| 6,616,451 B1 | 9/2003 | Rizoiu et al. |
| 6,942,658 B1 | 9/2005 | Rizoiu et al. |
| 7,090,047 B1 | 8/2006 | Lee et al. |
| 7,354,448 B2 | 4/2008 | Altshuler et al. |
| 2002/0095072 A1 | 7/2002 | Gonzales et al. |
| 2002/0177885 A1 | 11/2002 | Eisfeld et al. |
| 2003/0059379 A1 * | 3/2003 | Andersen et al. ............... 424/49 |
| 2003/0059738 A1 | 3/2003 | Neuberger |
| 2003/0232303 A1 | 12/2003 | Black |
| 2004/0010299 A1 | 1/2004 | Tolkoff et al. |
| 2004/0091834 A1 | 5/2004 | Rizoiu et al. |
| 2004/0191729 A1 | 9/2004 | Altshuler et al. |

(Continued)

FOREIGN PATENT DOCUMENTS

| EA | 8520 | 6/2007 |
| JP | H08-503383 | 4/1996 |

(Continued)

OTHER PUBLICATIONS

Bhatti et al., 1998, "A Study of the Uptake of Toluidine Blue O by Porphyromonas gingivalis and the Mechanism of Lethal Photosensitization", Photochemistry and Photobiology 68(3):370-376.

Dewhirst, 1980, "Structure-activity Relationships for Inhibition of Prostaglandin Cyclooxygenase by Phenolic Compounds", Prostaglandins, 20(2):209-222.

Hayek et al., 2005, "Comparative Study Between the Effects of Photodynamic Therapy and Conventional Therapy on Microbial Reduction in Ligature-Induced Peri-Implantitis in Dogs", Journal of Periodontology 76(8):1275-1281.

(Continued)

*Primary Examiner* — Frederick Krass
*Assistant Examiner* — Tracy Liu

(57) ABSTRACT

Generally regarded as safe (GRAS) dyes can be used as photosensitizing dyes in oral compositions to provide antibacterial and anti-inflammatory efficacy. Embodiments include oral care compositions including photosensitizing dyes, methods of making the compositions, methods of using the compositions, and kits containing the compositions and light emitting devices.

21 Claims, No Drawings

(56) References Cited

U.S. PATENT DOCUMENTS

| | | | |
|---|---|---|---|
| 2004/0193235 A1 | 9/2004 | Altshuler et al. | |
| 2005/0053898 A1* | 3/2005 | Ghosh et al. | 433/215 |
| 2005/0059731 A1 | 3/2005 | Albrecht et al. | |
| 2006/0019214 A1 | 1/2006 | Lawrence et al. | |
| 2006/0093561 A1 | 5/2006 | Kennedy | |
| 2006/0141422 A1 | 6/2006 | Philp et al. | |
| 2006/0281042 A1 | 12/2006 | Rizoiu et al. | |
| 2006/0282133 A1 | 12/2006 | Jensen | |
| 2006/0283478 A1 | 12/2006 | Avila et al. | |
| 2007/0003905 A1 | 1/2007 | Nguyen et al. | |
| 2007/0072153 A1 | 3/2007 | Gross et al. | |
| 2007/0123520 A1 | 5/2007 | Wood et al. | |
| 2007/0224570 A1 | 9/2007 | West et al. | |
| 2007/0237726 A1* | 10/2007 | White et al. | 424/49 |
| 2007/0237728 A1 | 10/2007 | Verheyen | |
| 2007/0259310 A1 | 11/2007 | Goodson et al. | |
| 2008/0039828 A1 | 2/2008 | Jimenez et al. | |
| 2008/0060148 A1* | 3/2008 | Pinyayev et al. | 15/22.1 |
| 2008/0233541 A1 | 9/2008 | De Vreese et al. | |
| 2008/0256729 A1 | 10/2008 | Link | |
| 2008/0286713 A1 | 11/2008 | Nanda | |
| 2008/0318178 A1 | 12/2008 | Abolfathi et al. | |
| 2009/0035725 A1 | 2/2009 | Loebel et al. | |
| 2009/0083924 A1 | 4/2009 | Shepherd et al. | |
| 2009/0130030 A1* | 5/2009 | Ribi | 424/49 |
| 2009/0285766 A1 | 11/2009 | Kishen et al. | |

FOREIGN PATENT DOCUMENTS

| | | |
|---|---|---|
| JP | 2005-503422 | 2/2005 |
| JP | 2008-534148 | 8/2008 |
| RU | 2162719 | 2/2001 |
| RU | 2296595 | 4/2007 |
| WO | WO 99/04628 | 2/1999 |
| WO | WO 99/43387 | 9/1999 |
| WO | WO 2004/037287 | 5/2004 |
| WO | WO 2006/107362 | 10/2006 |
| WO | WO 2006/135344 | 12/2006 |
| WO | WO 2007/127894 | 11/2007 |
| WO | WO 2009/047669 | 4/2009 |
| WO | WO 2009/047699 | 4/2009 |
| WO | WO 2009/047699 A1 | 4/2009 |
| WO | WO 2009/080850 | 7/2009 |
| WO | WO 2011/079075 | 6/2011 |
| WO | WO 2011/084744 | 7/2011 |

OTHER PUBLICATIONS

Lim et al., 2007, "The Anti-inflammatory Mechanism of 635 nm Light-emitting-diode Irradiation Compared with Existing COX Inhibitors", Lasers in Surgery and Medicine 39(7):614-621.

Luk et al., 2004, "Effect of Light Energy on Peroxide Tooth Bleaching", Journal of the American Dental Association 135:194-201.

Nomura et al., 2001, "Inhibition of Interleukin-1beta Production and Gene Expression in Human Gingival Fibroblasts by Low-energy Laser Irradiation", Lasers in Medical Science 16(3):218-223.

PCT/US2010/061325—ISR and Written Opinion mailed Jun. 1, 2011.

PCT/US2010/061325—Written Opinion mailed Dec. 2, 2011.

PCT/US2010/061329—ISR and Written Opinion mailed Apr. 26, 2011.

PCT/US2010/061329—Written Opinion mailed Dec. 19, 2011.

PCT/US2010/061332—ISR and Written Opinion mailed Feb. 18, 2011.

PCT/US2010/061332—Written Opinion mailed Dec. 19, 2011.

Redmond et al., 1999, "A Compilation of Singlet Oxygen Yields from Biologically Relevant Molecules", Photochemistry and Photobiology 70(4):391-475.

Riley et al., 2005, "An in-vitro Study of the Sterilization of Titanium Dental Implants using Low Intensity UV-radiation", Dental Materials 21(8):756-760.

Rovaldi et al., 2000, "Photoactive Porphyrin Derivative with Broad-Spectrum Activity against Oral Pathogens In Vitro", Antimicrobial Agents and Chemotherapy 44(12):3364-3367.

Sakurai et al., 2000, "Inhibitory Effect of Low-level Laser Irradiation on LPS-stimulated Prostaglandin $E_2$ Production and Cyclooxygenase-2 in Human Gingival Fibroblasts", Europen Journal of Oral Sciences 108(1):29-34.

Sarkar et al., 1993, "Lethal Photosensitization of Bacteria in Subgingival Plaque from Patients with Chronic Periodontitis", Journal of Periodontal Research 28(3):204-210.

Soukos et al., 1996, "Photodynamic Effects of Toluidine Blue on Human Oral Keratinocytes and Fibroblasts and *Streptococcus sanguis* Evaluated in vitro", Lasers in Surgery and Medicine 18(3):253-259.

Soukos et al., 2005, "Phototargeting Oral Black-Pigmented Bacteria", Antimicrobial Agents and Chemotherapy 49(4):1391-1396.

Soukos et al., 2006, "Photodynamic Therapy for Endodontic Disinfection", Journal of Endodontics, 32(10):979-984.

Sterer et al., 2005, "Effect of Visible Light on Malodour Production by Mixed Oral Microflora", Journal of Medical Microbiology 54(12):1225-1229.

Tech Light Systems, 2011 UltraBlu Toothbrush, www.ultrablu.net/order.html.

Usacheva et al., 2001, "Comparison of the Methylene Blue and Toluidine Blue Photobactericidal Efficacy Against Gram-positive and Gram-negative Microorganisms", Lasers in Surgery and Medicine 29(2):165-173.

Wainwright et al., 2004, "Photosensitising Agents—Circumventing Resistance and Breaking Down Biofilms: a review", Internation Biodeterioration & Biodegradation 53(2):119-126.

Wilson et al., 1995, "Bacteria in Supragingival Plaque Samples Can Be Killed by Low-power Laser Light in the Presence of a Photosensitizer", Journal of Applied Bacteriology 78(5):569-574.

Wood et al., 2006, "Erythrosine is a Potential Photosensitizer for the Photodynamic Therapy of Oral Plaque Biofilms", Journal of Antimicrobial Chemotherapy 57(4):680-684.

Hamblin et al., "Photodynamic therapy: a new antimicrobial approach to infectious disease?" Photochem. Photobiol. Sci. 2004, 3(5):436-50.

George et al., 2007, "Optimization of an advanced non-invasive light activated disinfection strategy," Proc. SPIE 6633, Biophotonics 2007: Optics in Life Science 663318-1.

Risovannaya, "Experimental Evaluation of the Bacteriotoxic Phototherapy of Inflammatory Diseases of the Oral Cavity," J. of Microbiology, Epidemiology and Immunobiology, 2005, p. 1-6 (English translation).

Risovannaya, "Experimental Evaluation of the Bacteriotoxic Phototherapy of Inflammatory Diseases of the Oral Cavity," J. of Microbiology, Epidemiology and Immunobiology, 2005, p. 1-6 (Russian language).

Verma et al., "Antimicrobial photodynamic efficacy of side-chain functionalized benzo [a] phenothiazinium dyes," Photochem Photobiol., 2009, 85(1):111-8; doi: 10.1111/j1751-1097.2008. 00403.x (Epub 2008) (Abstract only).

Risovannaya: "Experimental Evaluation of the Bacteriotoxic Phototherapy of Inflammatory Diseases of the Oral Cavity," J. of Microbiology, Epidemiology and Immunobiology, 2005, p. 1-6.

Verma S et al., "Antimicrobial photodynamic efficacy of side-chain functionalized benzo [a] phenothiazinium dyes," Photochem Photobiol. Jan.-Feb. 2009, 85(1):111-8.

Wilson et al., 1993, "Sensitization of periodontopathogenic bacteria to killing by light from a low-power laser," Oral Microbial Immunol., 8:182-187.

\* cited by examiner

KIT CONTAINING PHOTOSENSITIZING DYES

CROSS REFERENCE TO RELATED APPLICATIONS

This application is a national stage entry under 35 U.S.C. §371 of International Patent Application No. PCT/US2010/061329, filed 20 Dec. 2010, which claims priority to U.S. Provisional Patent Application Ser. No. 61/288,360, filed on 21 Dec. 2009, which are incorporated herein by reference.

BACKGROUND OF THE INVENTION

Dentifrice compositions are widely used in order to provide oral health. Dentifrices in the form of toothpaste, mouth rinses, chewing gums, edible strips, powders, foams, and the like have been formulated with a wide variety of active materials that provide a number of benefits to the user. Among these benefits are antimicrobial, anti-inflammatory, and anti-oxidant properties. These properties of dentifrices make them useful therapeutic agents to prevent or treat a number of oral health conditions such as cavities, gingivitis, plaque, tartar, periodontal disease, and the like.

Antibacterial agents used in dentifrice compositions typically have included chemicals or natural extracts. When developing suitable antibacterial agents a major problem that must be overcome is the uptake of the drug into the bacterial cell. Gram negative and Gram positive bacteria differ in the composition of their outer surface and respond differently to antimicrobial agents, especially in terms of uptake. Due to the high negatively charged surface of Gram negative bacteria they are relatively impeimeable to neutral or anionic drugs, including most commonly used photosensitisers.

It is known that certain organic compounds ("photosensitisers") can induce cell death by absorption of light in the presence of oxygen. The cytotoxic effect involves Type I and/or Type II photooxidation. Such photosensitisers find use in the treatment of cancer and other diseases or infections with light (photodynamic therapy or "PDT") and in the sterilisation (including disinfection) of surfaces and fluids by the light-induced destruction of microbes. It also is known that certain coloured phenothiazinium compounds, (e.g. methylene blue) can take part in Type I and Type II photooxidation processes, but compounds of this type thus far have proved unsuitable or of low efficacy as sensitisers for photodynamic therapy, or have shown low photochemical antimicrobial activity. For application in PDT, a good sensitiser must have at least some and preferably all of the following properties. Most importantly, it should cause the destruction of target cells (for example tumour cells or bacterial cells) efficiently on exposure to light. The PDT treatment using the photosensitiser should show a high degree of selectivity between target and normal tissues. The sensitiser should have relatively little dark toxicity and it should cause little or no skin photosensitivity in the patient. The sensitiser should have short drug to light intervals for patient and hospital convenience and to minimise treatment costs.

A number of different types of photosensitiser have been investigated in bacteria. These include phenothiazinium compounds, phthalocyanines, chlorins and naturally occurring photosensitisers. For uptake into Gram negative bacteria, it is accepted that the cationic derivatives are the most effective. Phenothiazinium compounds are blue dyes with maximum absorption at wavelengths between 600-700 nm. They have been studied for their non-photodynamic antibacterial properties but few apart from methylene blue and toluidine blue have been investigated photodynamically. Methylene blue and toluidine blue, however, are extremely toxic. Consequently, safer alternative photosensitizers would be desirable for use in oral care applications.

A variety of oral disorders (including plaque) are believed to be caused by bacteria. Gingivitis is the inflammation or infection of the gums and the alveolar bones that support the teeth. Gingivitis is generally believed to be caused by bacteria in the mouth (particularly the bacteria instigated in plaque formation) and the toxins formed as by-products from the bacteria. The toxins are believed to instigate oral tissue inflammation within the mouth. Periodontitis is a progressively worsened state of disease as compared to gingivitis, where the gums are inflamed and begin to recede from the teeth and pockets form, which ultimately may result in destruction of the bone and periodontal ligament. Bacterial infections of the structures that support the dentition can include gingivitis and periodontitis, but may also include infections of the bone, for example the mandibles as a result of surgical intervention. Further, oral tissue inflammation can be caused by surgery, localized injury, trauma, necrosis, improper oral hygiene or various systemic origins.

It is generally believed that the cellular components implicated by these diseases and conditions include epithelial tissue, gingival fibroblasts, and circulating leukocytes, all of which contribute to the host response to pathogenic factors generated by the bacteria. The most common bacterial pathogens implicated in these oral infections are *Streptococci* spp. (e.g., *S. mutans*), *Porphyromonas* spp., *Actinobacillus* spp., *Bacteroides* spp., and *Staphylococci* spp., *Fusobacterium nucleatum, Veillonella parvula, Actinomyces naeslundii*, and *Porphyromonas gingivalis*. Although the bacterial infection is often the etiological event in many of these oral diseases, the pathogenesis of the disease is mediated by the host response. Circulating polymorphonuclear neutrophils (PMNs) are largely responsible for the hyperactivity found at sites of infection. Typically PMNs and other cellular mediators of inflammation become hyper-functional and release toxic chemicals that are partly responsible for the destruction of tissue surrounding the foci of infection.

There are a variety of compositions described in the art for preventing and treating oral disorders that result from bacterial infection. In particular, to prevent the accumulation of inflammatory mediators derived from arachidonic acid pathway, non-steroidal anti-inflammatory drugs (NSAIDs) have been used successfully to treat patients suffering from periodontal disease and inflammatory diseases that are caused by arachidonic acid metabolites. Experimental and clinical data have shown that indomethacin, flurbiprofen, ketoprofen, ibuprofen, naproxen, and meclofenamic acid have significant ameliorative effects against alveolar bone loss, and reduction of prostaglandins and leukotrienes in dental disease models. However, one major disadvantage to the regular use of NSAIDs is the potential development of heartburn, gastric ulcers, gastrointestinal bleeding, and toxicity.

Other treatment methods include the use of antimicrobial therapeutics and antibiotics to eliminate the underlying infection. Certain antibiotics and other antimicrobial therapeutics potentially cause ulceration of oral mucous membranes, induction of desquamative gingivitis, discoloration, the potential for antibiotic resistance after prolonged usage, as well as exacerbation of tissue inflammation due to irritation.

It has been proposed to use light of varying wavelengths and intensities to whiten teeth, treat plaque, and/or to attach to bacteria and reveal the bacteria upon irradiation so that concentrated areas of plaque can be seen by the user. It has been proposed to use light alone to treat the bacteria, or by using a photosensitizer, such as methylene blue or toluidine blue, together with a light source as an antibacterial. See, e.g., U.S. Pat. Nos. 5,611,793, 6,616,451, 7,090,047, 7,354,448, and U.S. Patent Application Publication Nos. 2004/0091834, 2006/0281042, 2006/0093561, and 2009/0285766, the disclosures of which are incorporated by reference herein in their entirety. Many of these systems either use laser light, which is inherently dangerous, or light having a wavelength and intensity that generates undesirable heat either for the user or on the surface of the oral cavity. Thus, there exists a need to develop photosensitive compositions that are safe and effective, and that utilize relatively low intensity light sources that do not cause damage to the user's hand or oral cavity upon use.

SUMMARY OF THE INVENTION

It has now been found that generally regarded as safe (GRAS) dyes, while used conventionally in oral care compositions as colorants, possess strong anti-bacterial activity when irradiated with absorbable, visible light, and that the anti-bacterial activity is administered very rapidly, preferably in less than 2 minutes. The inventors also have found that in the absence of irradiatation, the GRAS dyes described herein are silent and exhibit little or no anti-bacterial activity. However, their anti-bacterial properties are turned on in the presence of absorbable, visible light.

In accordance with a feature of an embodiment, there is provided an optically clear oral composition comprising at least one photosensitizing dye, an oxygen generator or oxygen carrier, and an orally acceptable and optically clear carrier. In accordance with another embodiment, the orally acceptable carrier has a refractive index substantially similar to saliva to provide an oral composition having a refractive index substantially similar to saliva.

The present invention also provides a use of an optically clear oral composition according to any aspect of the present invention in the manufacture of a medicament for treating and/or preventing conditions caused by microorganisms in a subject, the treatment and/or prevention comprising: a) administering the optically clear oral composition; and b) irradiating the area to which the composition is administered with light at a wavelength absorbed by at least one photosensitizing dye.

The composition may be useful in treating and/or preventing conditions caused by microorganisms in the oral cavity of a subject. For example, the compositions may be useful for treating and/or preventing periodontal, gingival and/or halitosis conditions. For example, the conditions include, but are not limited to, gingivitis, plaque formation, cavity formation, periodontitis, dental caries, root caries, root canal infection, apical periodontitis, and the like. The composition also may be useful for managing bacteria deep within dental caries lesions, or to eliminate bacterial biofilm.

Certain embodiments of the invention also include a method of treating and/or preventing conditions caused by microorganisms in a subject, wherein the method comprises irradiating an area of the oral cavity suspected of containing microorganisms with visible light at a wavelength from 380 nm to 780 nm, at a dosage of from 1 J/cm² to 450 J/cm², with a power density of from about 1 to about 500 mW/cm², and for a period of time of from 1 second to 120 minutes. Another embodiment includes administering a photosensitizing dye to the oral cavity, and then irradiating the area to which the dye was administered with light. This embodiment therefore includes a) administering an optically clear oral care composition of any aspect of the present invention; and b) irradiating the area to which the composition is administered with light at a wavelength absorbed by the at least one photosensitizing dye. In some embodiments, the method encompasses simply irradiating inflamed tissue or tissue containing bacteria with light at a wavelength sufficient to reduce inflammation and/or reduce or eliminate the bacteria.

The method may be for treating and/or preventing conditions caused by microorganisms in the oral cavity of a subject. For example, the method may be for treating and/or preventing periodontal, gingival and/or halitosis conditions. For example, the conditions include, but are not limited to, gingivitis, plaque formation, cavity formation, periodontitis dental caries, root caries, root canal infection, apical periodontitis and the like. The method also may be for managing bacteria deep within dental caries lesions, or to eliminate bacterial biofilm.

The at least one photosensitizing dye may be included in the optically clear oral care composition in amounts. The irradiation procedure may be carried out for a time period of 120 minutes or less. For example, the irradiation may be carried out for 1 second to 120 minutes, and in some instances, between 2 seconds and 15 minutes. The time period for carrying out the irradiation depends on the type of photosensitizing dye used, and the type of light used.

In some embodiments, the light used in the irradiation process typically has a wavelength within the range of from 380 nm to 1450 nm, and more preferably from 400 nm to 780 nm. The dose of light used in step (b) may range from 1 J/cm² to 450 J/cm², with a power density of from 1 to 500 mW/cm².

In accordance with another embodiment, the present invention also provides a kit for treating and/or preventing conditions caused by microorganisms in a subject, the kit comprising an optically clear oral care composition according to any aspect of the invention, disposed in at least one suitable container. The kit may further comprise a light emitting device capable of emitting light at the appropriate wavelength, in the appropriate dosage and with the appropriate power. The light emitting device may be included within an applicator that is capable of applying the optically clear oral care composition to the oral cavity, and then also capable of irradiating the area to which the composition is administered. The kit may be useful for treating and/or preventing conditions caused by microorganisms in the oral cavity of a subject. For example, the kit may be useful for treating and/or preventing periodontal, gingival, and/or halitosis conditions. The conditions include and of the aforementioned conditions, and the kit may be used for managing bacteria deep within dental caries lesions, or to eliminate bacterial biofilm.

In accordance with another feature of an embodiment of the invention, there is provided a method of preparing the optically clear oral care composition according to any aspect of the invention. The method may comprise: a) preparing an orally acceptable and optically clear carrier by mixing the components of the carrier in a manner that adequately disperses the components to result in a carrier that is optically clear; and b) adding at least one photosensitizing dye to the mixture of a).

The embodiments provide a number of advantages over known antibacterial treatments. The embodiments do not make use of toxic or unsafe photo sensitizers. The embodiments also provide effective antibacterial treatment using lower powered light in the visible spectrum that is safer than lasers or other high-powered light emitting devices. In addition, a lower concentration of active ingredient (GRAS dye/photosensitizer) can be used in the periodontal pocket unlike the high concentrations required for many hours with conventional antimicrobials. This is an important distinction over prior art of using anti-microbials in oral care where they are predominately depleted over time. The photosensitizer can be repeatedly used like a catalyst to produce enough singlet oxygen or other radical species for anti-microbial benefit. These and other advantages can be obtained through use of the embodiments described herein.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following definitions and non-limiting guidelines must be considered in reviewing the description of this invention set forth herein. The headings (such as "Background" and "Summary,") and sub-headings (such as "Compositions" and "Methods") used herein are intended only for general organization of topics within the disclosure of the invention, and are not intended to limit the disclosure of the invention or any aspect thereof. In particular, subject matter disclosed in the "Background" may include aspects of technology within the scope of the invention, and may not constitute a recitation of prior art. Subject matter disclosed in the "Summary" is not an exhaustive or complete disclosure of the entire scope of the invention or any embodiments thereof. Classification or discussion of a material within a section of this specification as having a particular utility (e.g., as being an "active" or a "carrier" ingredient) is made for convenience, and no inference should be drawn that the material must necessarily or solely function in accordance with its classification herein when it is used in any given composition.

The citation of references herein does not constitute an admission that those references are prior art or have any relevance to the patentability of the invention disclosed herein. Any discussion of the content of references cited in the Introduction is intended merely to provide a general summary of assertions made by the authors of the references, and does not constitute an admission as to the accuracy of the content of such references.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations the stated of features. Specific Examples are provided for illustrative purposes of how to make and use the compositions and methods of this invention and, unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention. In addition, the compositions and the methods may comprise, consist essentially of, or consist of the elements described therein.

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material. The recitation of a specific value herein, whether referring to respective amounts of components, or other features of the embodiments, is intended to denote that value, plus or minus a degree of variability to account for errors in measurements. For example, an amount of 10% may include 9.5% or 10.5%, given the degree of error in measurement that will be appreciated and understood by those having ordinary skill in the art.

As used herein, "antibacterial activity" herein means activity as determined by any generally accepted in vitro or in vivo antibacterial assay or test. "Anti-inflammatory activity" herein means activity as determined by any generally accepted in vitro or in vivo assay or test, for example an assay or test for inhibition of prostaglandin production or cyclooxygenase activity. "Antioxidant activity" herein means activity as determined by any generally accepted in vitro or in vivo antioxidant assay or test.

An "oral surface" herein encompasses any soft or hard surface within the mouth including surfaces of the tongue, hard and soft palate, buccal mucosa, gums and dental surfaces. A "dental surface" herein is a surface of a natural tooth or a hard surface of artificial dentition including a crown, cap, filling, bridge, denture, dental implant and the like. The term "inhibiting" herein with respect to a condition such as inflammation in an oral tissue encompasses prevention, suppression, reduction in extent or severity, or amelioration of the condition.

An oral care composition of the present invention can take any form suitable for application to an oral surface. In various illustrative embodiments the composition can be a liquid solution suitable for irrigating, rinsing or spraying; a dentifrice such as a powder, toothpaste or dental gel; a periodontal gel; a liquid suitable for painting a dental surface (e.g., a liquid whitener); a chewing gum; a dissolvable, partially dissolvable or non-dissolvable film or strip (e.g., a whitening strip); a bead (e.g., composition encapsulated in gelatin), a wafer; a lozenge, a wipe or towelette; an implant; a mouthrinse, a foam, a dental floss; etc. The composition can contain active and/or carrier ingredients additional to those recited above.

Preferred oral care compositions include those selected from dentifrices, oral rinses, oral strips, lozenges, beads, liposomes, micelles, reverse micelles, micro- or nano-encapsulated containers, enzymes, proteins, bacteria targeting peptides/small molecules, gels, sol-gels, hydrogels, silicas, organic zeolites, inorganic silicas such as those present in dentifrice, paint-ons, oral patches, polymers, sprays, smoke inhalatation devices, foams, chewing gums, from the back or through a toothbrush head, oils or other products used for oral hygiene or benefit. These products can also include food stuffs, liquids and probiotics that endogenously contain or can be laced with photoabsorbing species for oral treatment.

Throughout this description, the expression "optically clear" denotes a material that has a clarity close to or equal to a clear or transparent material, even though the composition may be colored. The clarity preferably is determined by measuring the total luminance transmission and/or the haze (% of scattered transmitted visible light) through the total thickness of the composition. Total luminance transmission in the range 80 to 100, and particularly from 88 to 95, and haze in the range <3.5%, and particularly <2.5%, is preferred.

Optically clear compositions in accordance with the present invention also preferably do not significantly reduce the light density, when compared to light transmission through a clear apparatus (e.g., a clear film or glass). For example, the amount of light transmitted through the oral care composition can be reduced by less than 40%, preferably less than 25%, and more preferably less than 10%, when compared to the amount of light transmitted through a clear slide glass. The amount of light transmitted through a dentifrice slurry when the photosensitizing dye were used may be reduced by less than 20%, more preferably, less than 10%, most preferably less than 8%, when compared to the amount of light transmitted through a clear apparatus. In some instance, the light transmitted through a dentifrice slurry when the photosensitizing dye were used may be increased, not reduced.

Classification herein of an ingredient as an active agent or a carrier ingredient is made for clarity and convenience, and no inference should be drawn that a particular ingredient necessarily functions in the composition in accordance with its classification herein. Furthermore, a particular ingredient can serve a plurality of functions, thus disclosure of an ingredient herein as exemplifying one functional class does not exclude the possibility that it can also exemplify another functional class.

The embodiments described herein include an optically clear oral composition comprising at least one photosensitizing dye, an oxygen generator or oxygen carrier, and an orally acceptable and optically clear carrier. Other embodiments contemplate an oral composition as described above, except the orally acceptable carrier has a refractive index substantially similar to saliva to provide an oral composition having a refractive index substantially similar to saliva.

The oral care compositions described herein preferably are comprised of ingredients that limit the amount and degree of light scatter. This will minimize the optical dosage needed for anti-bacterial or anti-gingivitis efficacy, thereby reducing the optical density and the overall power consumption required for powering the light in the oral light device. In one embodiment, for example, the dentifrice will be optically clear, and in another embodiment, the refractive index of the formulation slurry will closely match that of the saliva in the oral cavity. Ingredients that can be used to index match will be therefore be particularly beneficial in the dentifrice, for example, sorbitol, glycerin, polyethylene glycol (PEG) 600. Abrasive and opacifying ingredients such as silica should preferably be reduced to a minimum (typically less than 3% by weight) or be replaced with other less opaque abrasives such as clear, abrasive hydrogel microspheres and/or beads. The dentifrice preferably is comprised of ingredients that enhance light transmission at the desired wavelength(s) of light, and/or do not significantly reduce the transmission of light.

The oral care compositions also may contain an oxygen generator or oxygen carrier. The oxygen generator is a compound that can produce oxygen, and an oxygen carrier is a compound that can transport oxygent, both of which serve to enhance oxygen availability and therefore the yield of the singlet excited state. Suitable oxygen generators or oxygen carriers include for example, hydrofluoro carbons, perfluoro carbons, or mixtures thereof. Suitable compounds include, but are not limited to, perfluorodecahydro naphthalene, perfluorodecalin, perfluorohexane, octafluoropropane, perfluorobutane, perfluorooctane, perfluorodecane, perfluoromethyldecalin, dilute sodium hypochlorite, hydrogen peroxide and other peroxides, DMSO, chlorine dioxide, and mixtures thereof. Ingredients useful in the compositions described herein also preferably increase the lifetime of the triplet state of the photosensitizing dye, or quantum yield of the photosensitizing dye.

The formulation preferably is made with ingredients that will aid the binding and/or delivery of the photosensitizing dye to the desired destination, either the hard and/or soft-tissue of the oral cavity containing the biofilm. For example, bacteria targeting proteins, peptides, and other molecules can be used to transport the dye to the site of bacteria. This aspect of the embodiments is especially useful when the bacteria is present in hard to reach sites in the oral cavity. In one embodiment the photosensitizing dye may be incorporated into a food or gum, or food stuffs rich in such dyes might be used. Examples of foodstuffs known to contain photosensitizers (e.g., photosensitizing dyes) include but are not limited to, parsley, parsnips, tomatoes, and carrots.

The photosensitizing dye also may be water soluble and dispersed throughout the dentifrice or be contained in beads, strips or small containers scattered throughout the dentifrice. Dentifrice flavor ingredients can be used that are stable to the wavelength and optical dosage of the light used, and to the photosensitizer. The flavors preferably are not be absorbed by the wavelength of light. In addition, dentifrices may contain more than one photosensitizing dye or photosensitizer to impart different consumer acceptable colors. The dentifrice formulation might contain, for example, titanium oxide to lighten the intensity of the color to the consumer while still retaining the same concentration of the GRAS dye. If titanium dioxide is used, however, it should be used in amounts low enough to maintain the optical clarity of the composition.

The photosensitizing dyes useful in the present invention preferably have one or more of the following charcteristics. It is preferred that the dyes have a high extinction coefficient (>10 L mol$^{-1}$ cm$^{-1}$. For example, the molar extinction coefficient of riboflavin is aboutl 0,000; and beta-carotene, 180, 000 L mol$^{-1}$ cm$^{-1}$). The dyes preferably have a high quantum yield (0.05 max. 1.0) for its triplet excited energy state. In addition, the dyes should have a triplet energy lifetime long enough to permit generation of highly, reactive cytotoxic species for destruction of the microbe. Finally, it is preferred that the dyes have high product yields for singlet oxygen $^1O_2$, superoxide $O_2^-$ and other destructive free-radicals or non-radical species. Typical quantum yields of photosensitizers, rates and yields for intersystem crossing and formation of singlet oxygen are described in "A compilation of singlet oxygen yields from biologically relevant molecules" Photochemistry & Photobiology, 1999, 70(4), 391-475.

Other useful features of the photosensitizing dyes include the following. The dyes should be toxic only upon photoactivation, and should have minimal dark toxicity. The dyes should provide low systemic toxicity, be selectively and rapidly localized and retained by the target microbe for repeated cycles of photoirradiation with no photobleaching. The dyes also should provide little or no staining of hard or soft tissue to avoid any adverse side effects or undesirable cosmetic staining. The dyes also should not be absorbed or quenched to any appreciable degree by other species in the cell, oral cavity or while in product formulation. It also is preferred that the photosensitizing dyes be chemically pure and of known composition.

Any photosensitizing dye having one or more of the above-identified characteristics can be used in the embodiments of the invention. The photosensitizing dyes are those that are generally regarded as safe, or GRAS, and consequently, exclude normally toxic dyes such as methylene blue or toluidine blue. Photosensitizers for use in this invention can have a maximum absorption wavelength between 380 nm onwards. Actives can also be fluorescent. Actives that may exhibit phosphorescene may be particularly beneficial as their high triplet energies lifetimes will translate to increased efficiency in transferring its energy to ground state oxygen and therefore a corresponding increase in the yield of singlet oxygen, which will lead to an increase in the efficiency of the light therapy. Representative GRAS compounds for use in this invention are shown in Table 1 below.

phyrin tetracarboxyl porphyrin, Herderoporphyrin tricarboxyl porphyrin, Protoporphyrin dicarboxyl porphyrin, and mixtures thereof.

Additional compounds that also can may function as new, anti-bacterial actives, though not all necessary GRAS, for use in the eradication of microbes, are disclosed in, for example, Photochemistry & Photobiology, 1999, 70(4), 391-475 "A compilation of singlet oxygen yields from biologically relevant molecules". Some known photosensitizer that could be used in the present invention are listed in Table 2 below

TABLE 1

| Photosensitizing Dyes (GRAS) | | |
|---|---|---|
| GRAS Compound (Photosensitizing Dyes) | Wavelength/nm | Typically Present in Oral Care Products |
| Chlorophyllin sodium copper salt | 405 | Used at up to 0.03% |
| Tartrazine (FD&C Yellow No. 5) | max. 426 in water | Used at up to 0.004% |
| Curcumin | max. 427 | |
| Riboflavin 5'-monophosphate sodium salt | 441 | |
| Allura Red AC (FD&C Red No. 40) | max. 504 | Used at up to 0.14% |
| New Coccine (CI 16255, Food Red 7) | max. 350 (2nd), max. 506 | Used at upto 0.02% |
| Chromotrope FB (CI 14720, Food Red 3) | max. 383, max. 515 (2nd) | Used at upto 0.6% |
| Indigo Carmine | max. 608 | |
| Erioglaucine disodium salt (FD&C Blue No. 1) | max. 408, max. 629 (2nd) | Used at up to 0.3% |
| Fast Green FCF (FD&C Green No. 3) | max. 625 | Used at upto 0.0011% |
| Lissamine Green B | max. 633 | |
| Napthol Green or Acid Green | — | |
| Cochineal | 530 | |
| Carmoisine azorubine | 515 | |
| Amaranth | 523 | |
| Brillant Scarlet 4R | 503 | |
| Chlorophylls and copper complexes | 633 | |
| Brillant black BN (PN) | — | |
| Chocolate Brown HT | — | |
| Beta-carotene | 470 | |
| Bixin | — | |
| Lycopene | 530 | |
| Betanin | — | |
| Riboflavin | 445 | |
| Riboflavin 5'-monophosphate sodium salt | 441 | |
| Erythrosin B sodium salt | max. 525 at pH 7 | Used at upto 0.007% |
| $TiO_2$ Anatase P25 Degussa | at 578 nm inhibits S. Mutans | |

Anthocyanins as a general class of compounds that also may be used for light-triggered eradication of bacteria. Many anthocyanins are used as food additives. In fact, the colors used in soft drinks such as Kool Aid™ that contain many different food dye additives also may be used in combination with light to eradicate bacteria. Hence, the use of mouth rinses that are rich in such compounds can be used in conjunction with light to provide effective oral hygiene. Natural food colors, lake food colors, synthetic food colors can all be harnessed to help eradicate bacteria through the specific use of desired wavelengths of light, optical power and irradiation time.

Endogenous chromophores present in bacteria also may be added to the delivery vehicle whether it be dentrifrice or mouth rinse to boost the efficiency and effectiveness of the light-mediated eradication of bacteria. Endogenous chromophores such as porphyrins would include, for example, Uroporphyrin octacarboxyl, Heptacarboxyl porphyrin, Hexacarboxyl porphyrin, Pentacarboxyl porphyrin, Co-por-

TABLE 2

| Photosensitiser type | Wavelength range (nm) |
|---|---|
| Acridine | 400-500 |
| Phenazine | 500-550 |
| Cyanine | 500-900 |
| Phenothiazinium | 590-670 |
| Porphyrin | 600-690 |
| Phthalocyanine | 660-700 |

Thus, the photosensitizing dye may be selected from the group consisting of Chlorophyllin sodium copper salt, Tartrazine (FD&C Yellow No. 5), Curcumin, Riboflavin 5'-monophosphate sodium salt, Allura Red AC (FD&C Red No. 40), New Coccine (CI 16255, Food Red 7), Chromotrope FB (CI 14720, Food Red 3), Indigo Carmine, Erioglaucine disodium salt (FD&C Blue No. 1), Fast Green FCF (FD&C Green No. 3), Lissamine Green B, Napthol Green or Acid Green, Cochineal, Carmoisine azorubine, Amaranth, Brillant Scarlet 4R, Chlorophylls and copper complexes, Brillant black BN(PN), Chocolate Brown HT, Beta-carotene, Bixin, Lycopene, Betanin, Riboflavin, Erythrosin B sodium salt, $TiO_2$ Anatase P25 Degussa, anthocyanins, Uroporphyrin octacarboxyl, Heptacarboxyl porphyrin, Hexacarboxyl porphyrin, Pentacarboxyl porphyrin, Co-porphyrin tetracarboxyl porphyrin, Herderoporphyrin tricarboxyl porphyrin, Protoporphyrin dicarboxyl porphyrin, acridine, phenazine, cyanine, phenothiazinium, porphyrin, phthalocyanine, and mixtures thereof.

It is preferred that the photosensitizing dye be selected from the group consisting of Chlorophyllin sodium copper salt, Tartrazine (FD&C Yellow No. 5), Curcumin, Riboflavin 5'-monophosphate sodium salt, Allura Red AC (FD&C Red No. 40), New Coccine (CI 16255, Food Red 7), Chromotrope FB (CI 14720, Food Red 3), Indigo Cannine, Erioglaucine disodium salt (FD&C Blue No. 1), Fast Green FCF (FD&C Green No. 3), Lissamine Green B, Napthol Green or Acid Green, Cochineal, Carmoisine azorubine, Amaranth, Brillant Scarlet 4R, Chlorophylls and copper complexes, Brillant black BN(PN), Chocolate Brown HT, Beta-carotene, Bixin, Lycopene, Betanin, Riboflavin, Erythrosin B sodium salt, and mixtures thereof. More preferably, the photosensitizing dye is selected from Tartrazine, Curcumin, Allura Red, Fast Green FCF, and mixtures thereof.

The photosensitizing dye may be present in the optically clear oral care compositions in a concentration effective to provide an anti-bacterial effect, when irradiated with the appropriate wavelength of light for the appropriate amount of time and at the appropriate dosage and power density. Preferably, the dye is present in an amount ranging from 0.0001 to 2.0% by weight, based on the total weight of composition. More preferably, the dye is present in an amount ranging from 0.001 to 1.0% by weight, and even more preferably from 0.05 to 0.5% by weight.

Any suitable light may be used for the irradiation procedure. For example, a low powered light source or a diode laser source may be used. Any suitable light such as visible or infrared lasers may be used. High energy non-visible light such as tungsten halogen or xenon arc source may also be used. LED light sources may also be used. The advantage of using LED light sources is that it will reduce the potential for the generation of uncomfortable heat, and therefore cause less discomfort to the subject. The irradiation procedure may be performed for the whole of the affected area. In particular, irradiation preferably is performed for the whole interior of the mouth. For example, the light source may be manipulated such that accessible interior surfaces are irradiated. Alternatively, only some areas are irradiated. For example, individual pockets of areas may be irradiated. The light source may be adapted to irradiate all regions of the oral cavity, including under the tongue and through the flesh covered lingual, labial, anterior and posterior areas of the oral cavity and through the bite surface.

Preferably, the light source emits light having a wavelength within the range of from 380 nm to 1450 nm, and more preferably from 400 nm to 780 nm (i.e., the visible spectrum). The dose of light used in step (b) may range from 1 $J/cm^2$ to 450 $J/cm^2$, with a power density of from 1 to 500 $mW/cm^2$. It is preferred that the light source be in the form of a light emitting diode (LED) with dose and power densities sufficient to activate the photosensitizing dyes, but yet not so powerful as to damage the treated area. LEDs are preferred because various wavelengths of light (typically varying by 10 nm) and various optical power outputs can be achieved by varying the current to the LED with an external power supply.

The wavelength of light used will vary depending on the maximum wavelength of absorption of the photosensitizing dye. In the event a photosensitizing dye possesses more than one prominent absorption band, the dyes can be excited at those wavelengths, either individually or sequentially, one absorption wavelength after another, or simultaneously with multiple wavelengths of light. It may be preferred in some instances to pulse the light, especially when emitting light at a high dosage limits the degree of anti-bacterial efficacy derived from singlet oxygen or other oxygen dependant reactive moieties by generating singlet oxygen at a rate the depletes oxygen faster than it can be replenished. The use of the oxygen generator or oxygen carrier preferably enhances the anti-bacterial action with light.

The compositions of the embodiments preferably are irradiated with the appropriate wavelength of light for 120 minutes or less. For example, the irradiation may be carried out for 1 second to 120 minutes, and in some instances, between 2 seconds and 15 minutes. The compositions preferably are irradiate with the appropriate wavelength of light at an energy dose between 1 and 450 $J/cm^2$, more preferably between 1 and 100 $J/cm^2$, more preferably from 10 to 50 $J/cm^2$, and most preferably from 15 to 45 $J/cm^2$. The compositions slao preferably are irradiate with the appropriate wavelength of light having an optical power density of from 1 to 500 $mW/cm^2$, more preferably from 1 to 400 $mW/cm^2$, even more preferably from 1 to 50 $mW/cm^2$, and most preferably from 3 to 15 $mW/cm^2$.

Any device suitable of emitting light at the above-mentioned wavelengths, energy dosage, and optical power can be used, including toothbrushes, miniature toothbrushes, small pencil or pen-shaped devices. Alternative light sources include light emitting treatment devices capable of irradiating large portions of the oral cavity at once, such as those described in U.S. Pat. Nos. 5,487,662, 4,867,682, 5,316,473, 4,553,936, and in U.S. Patent Applicaton Publication Nos. 2006/0093561, 2006/0281042, 2004/0091834, and 2009/0285766, the disclosures of each of which are incorporated by reference herein in their entirety. Other light emitting treatment devices that can be manually manipulated to deliver light to various regions in the mouth which can be used include fibre optic wands, guns or light guides, remote light engines utilizing light generation means in the form of quartz halogen, mercury xenon, xenon, metal halide, sulfur based or other light emitting diode (LED) technology, flexible lightpipes composed of a number of individual fiber optic elements or liquid lightpipes, and other dental impression trays containing light emitting diodes. While various light devices may be used, it will be appreciated that the light device should be capable of delivering an effective dose of light at an effective wavelength. Thus, higher intensities may be used in combination with pulsed light delivery, or lower intensities with continuous light delivery. The spectrum of light emitted by the light emitting treatment device would be selected to match the particular absorption curve of the photosensitizing dye used. A bandpass filter could be used to eliminate wavelengths not absorbed by the photosensitizes.

Preferred light emitting treatment devices are expected to be LED based, and can be made into a variety of shapes that will be comfortable for patients and simple to apply for dentists and/or dental hygienists. It is expected that a suitable light device can be made from a standard dental mouth plate carrying an encapsulated scattering gel (as is known in the art), which gel is pressed up against the gums when the device is in use. LEDs can be embedded directly into the gel and positioned to face the gingival tissue. The scattering medium should ensure that the light is delivered in a uniform cross-section to the gingival tissue surface. Electronic connections to the LEDs can be made to the dental plate out from the front of the mouth. Alternatively, it is contemplated that the light source may be in the form of optical fibers or other light guides coupled to LEDs with their terminus within the scattering gel.

Certain embodiments of the invention include a method of treating and/or preventing conditions caused by microorganisms in a subject, wherein the method comprises: a) administering an optically clear oral care composition as described herein; and b) irradiating the area to which the composition is administered with light at a wavelength absorbed by the at least one photosensitizing dye, and for an effective period of time at an appropriate dosage and optical power density.

The method may be for treating and/or preventing conditions caused by microorganisms in the oral cavity of a subject. For example, the method may be for treating and/or preventing periodontal, gingival and/or halitosis conditions. For example, the conditions include, but are not limited to, gingivitis, plaque formation, cavity formation, periodontitis dental caries, root caries, root canal infection, apical periodontitis and the like. The method also may be for managing bacteria deep within dental caries lesions, or to eliminate bacterial biofilm.

The embodiments described herein also envision a kit for treating and/or preventing conditions caused by microorganisms in a subject, the kit comprising an optically clear oral care composition as described herein, disposed in at least one suitable container. The kit may further comprise a light emitting device capable of emitting light at the appropriate wavelength, in the appropriate dosage and with the appropriate optical power density. The light emitting device may be included within an applicator that is capable of applying the optically clear oral care composition to the oral cavity, and then also capable of irradiating the area to which the composition is administered. The kit may be useful for treating and/or preventing conditions caused by microorganisms in the oral cavity of a subject. For example, the kit may be useful for treating and/or preventing periodontal, gingival, and/or halitosis conditions. The conditions include and of the aforementioned conditions, and the kit may be used for managing bacteria deep within dental caries lesions, or to eliminate bacterial biofilm.

Additional features of the invention include a method of preparing the optically clear oral care composition by: a) preparing an orally acceptable and optically clear carrier by mixing the components of the carrier in a manner that adequately disperses the components to result in a carrier that is optically clear; and b) adding at least one photosensitizing dye to the mixture of a).

In various embodiments, the optically clear compositions may be formulated with conventional dentifrice components, including, for example, at least one humectant, at least one abrasive material, and the like. In various embodiments, the optically clear oral care compositions do not include additional antibacterial agents, although their use is optional. In the event additional antibacterial agents are used, the compositions may further comprise an antibacterial agent selected from the group consisting of natural extracts, cetyl pyridinium chloride, polyphenols, phenolic compounds, stannous ions, zinc ions, and the like.

The compositions described herein may be formulated with optional other ingredients, including without limitation anticaries agent, anticalculus or tartar control agents, anionic carboxylate polymers, viscosity modifiers, surfactants, flavorants, pigments, signals (flavor, color, light, heat, smell and other signals that signal the efficacious or advantageous use of the composition), agents to treat dry mouth, and the like. The addition of the optional ingredients is premised on the notion that the compositions should remain optically clear after their addition. That is, the ingredients should not adversely affect the optical clarity of the composition. The inventors discovered that silica abrasives in amounts greater than 6%, adversely affect the light absorbence of the compositions, and consequently, it is preferred to use from 1 to 6% silica abrasive, more preferably, from 1 to 4% silica abrasive, even more preferably from 1 to 3% silica abrasive, and most preferably less than 2% silica abrasive.

In various embodiments, the compositions comprise an orally acceptable source of fluoride ions, which serves as an anticaries agent. One or more such sources can be present. Suitable sources of fluoride ions include fluoride, monofluorophosphate and fluorosilicate salts as well as amine fluorides, including olaflur (N'-octadecyltrimethylendiamine-N,N,N'-tris(2-ethanol)-dihydrofluoride).

As anticaries agent, one or more fluoride-releasing salts are optionally present in an amount providing a total of 100 to 20,000 ppm, 200 to 5,000 ppm, or 500 to 2,500 ppm, fluoride ions. Where sodium fluoride is the sole fluoride-releasing salt present, illustratively an amount of 0.01% to 5%, 0.05% to 1% or 0.1% to 0.5%, sodium fluoride by weight can be present in the composition. Other anticaries agents can be used, such as arginine and arginine derivatives (e.g., ethyl lauroyl arginine (ELAH)).

Phenolic compounds useful herein illustratively include, subject to determination of oral acceptability, those identified as having anti-inflammatory activity by Dewhirst (1980), Prostaglandins 20(2), 209-222, but are not limited thereto. Examples of antibacterial phenolic compounds include 4-allylcatechol, p-hydroxybenzoic acid esters including benzylparaben, butylparaben, ethylparaben, methylparaben and propylparaben, 2-benzylphenol, butylated hydroxyanisole, butylated hydroxytoluene, capsaicin, carvacrol, creosol, eugenol, guaiacol, halogenated bisphenolics including hexachlorophene and bromochlorophene, 4-hexylresorcinol, 8-hydroxyquinoline and salts thereof, salicylic acid esters including menthyl salicylate, methyl salicylate and phenyl salicylate, phenol, pyrocatechol, salicylanilide, and thymol. These phenolic compounds typically are present in one or more of the natural extracts described above.

The at least one phenolic compound is optionally present in a total amount of 0.01% to 10% by weight. Illustratively the total concentration of the at least one phenolic compound in a toothpaste or gel dentifrice or mouth rinse of the present invention can be 0.01% to 5%, for example 0. 1% to 2%, 0.2% to 1% or 0.25% to 0.5%.

Other suitable antibacterial agents include, without limitation, copper (II) compounds such as copper (II) chloride, fluoride, sulfate and hydroxide, zinc ion sources such as zinc acetate, zinc citrate, zinc gluconate, zinc glycinate, zinc oxide, zinc sulfate and sodium zinc citrate, phthalic acid and salts thereof such as magnesium monopotassium phthalate, hexetidine, octenidine, sanguinarine, benzalkonium chloride, domiphen bromide, alkylpyridinium chlorides such as cetylpyridinium chloride (CPC) (including combinations of CPC with zinc and/or enzymes), tetradecylpyridinium chloride and N-tetradecyl-4-ethylpyridinium chloride, iodine, sulfonamides, bisbiguanides such as alexidine, chlorhexidine and chlorhexidine digluconate, piperidino derivatives such as delmopinol and octapinol, magnolia extract, grapeseed extract, menthol, geraniol, citral, eucalyptol, antibiotics such as augmentin, amoxicillin, tetracycline, doxycycline, minocycline, metronidazole, neomycin, kanamycin and clindamycin, and the like. A further illustrative list of useful antibacterial agents is provided in U.S. Pat. No. 5,776,435 to Gaffar et al., incorporated herein by reference. If present, these additional antimicrobial agents are present in an antimicrobial effective total amount, typically 0.05% to 10%, for example 0.1% to 3% by weight, of the composition.

In another embodiment the composition comprises an orally acceptable anticalculus agent. One or more such agents can be present. Suitable anticalculus agents include without limitation phosphates and polyphosphates (for example pyrophosphates), polyaminopropanesulfonic acid (AMPS), zinc citrate trihydrate, polypeptides such as polyaspartic and polyglutamic acids, polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts. Useful inorganic phosphate and polyphosphate salts illustratively include monobasic, dibasic and tribasic sodium phosphates, sodium tripolyphosphate, tetrapolyphosphate, mono-, di-, tri- and tetrasodium pyrophosphates, disodium dihydrogen pyrophosphate, sodium trimetaphosphate, sodium hexametaphosphate and the like, wherein sodium can optionally be replaced by potassium or ammonium. Other useful anticalculus agents include anionic polycarboxylate polymers. The anionic polycarboxylate polymers contain carboxyl groups on a carbon backbone and include polymers or copolymers of acrylic acid, methacrylic, and maleic anhydride. Non-limiting examples include polyvinyl methyl ether/maleic anhydride (PVME/MA) copolymers, such as those available under the Gantrez™ brand from ISP, Wayne, N.J. Still other useful anticalculus agents include sequestering agents including hydroxycarboxylic acids such as citric, fumaric, malic, glutaric and oxalic acids and salts thereof, and aminopolycarboxylic acids such as ethylenediaminetetraacetic acid (EDTA). One or more anticalculus agents are optionally present in the composition in an anticalculus effective total amount, typically 0.01% to 50%, for example 0.05% to 25% or 0.1% to 15% by weight.

In various embodiments, the anticalculus system comprises a mixture of sodium tripolyphosphate (STPP) and a tetrasodium pyrophosphate (TSPP). In various embodiments, the ratio of TSPP to STPP ranges 1:2 to 1:4. In a preferred embodiment, the first anticalculus active ingredient, TSPP is present at 1 to 2.5% and the second anticalculus active ingredient, STPP is present at 1 to 10%.

In one embodiment, the anionic polycarboxylate polymer is present 0.1% to 5%. In another embodiment, the anionic polycarboxylate polymer is present 0.5% to 1.5%, most preferably at 1% of the oral care composition. In one embodiment according to the present invention, the anticalculus system comprises a copolymer of maleic anhydride and methyl vinyl ether, such as for example, the Gantrez S-97 product discussed above.

In various embodiments, the ratio of TSPP to STPP to the synthetic anionic polycarboxylate ranges 5:10:1 to 5:20:10 (or 1:4:2). In one embodiment, the anticalculus system of the oral care composition comprises TSPP, STPP, and a polycarboxylate such as a copolymer of maleic anhydride and methyl vinyl ether at a ratio of 1:7:1. In a non-limiting embodiment, the anticalculus system consists essentially of TSPP present at 0.5% to 2.5%, STPP present at 1% to 10%, and a copolymer of maleic anhydride and methyl vinyl ether present at 0.5% to 1.5%

In another embodiment the composition comprises an orally acceptable stannous ion source useful, for example, in helping reduce gingivitis, plaque, calculus, caries or sensitivity. One or more such sources can be present. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of 0.01% to 10%, for example 0.1% to 7% or 1% to 5% by weight of the composition.

In another embodiment the composition comprises an orally acceptable zinc ion source useful, for example, as an antimicrobial, anticalculus or breath-freshening agent. One or more such sources can be present. Suitable zinc ion sources include without limitation zinc acetate, zinc citrate, zinc gluconate, zinc glycinate, zinc oxide, zinc sulfate, sodium zinc citrate and the like. One or more zinc ion sources are optionally and illustratively present in a total amount of 0.05% to 3%, for example 0.1% to 1%, by weight of the composition.

In another embodiment the composition comprises an orally acceptable breath-freshening agent. One or more such agents can be present in a breath-freshening effective total amount. Suitable breath-freshening agents include without limitation zinc salts such as zinc gluconate, zinc citrate and zinc chlorite, α-ionone and the like.

In another embodiment the composition comprises an orally acceptable antiplaque, including plaque disrupting, agent. One or more such agents can be present in an antiplaque effective total amount. Suitable antiplaque agents include without limitation stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and chelating agents such as citric and tartaric acids and alkali metal salts thereof.

In another embodiment the composition comprises an orally acceptable anti-inflammatory agent other than the rosemary components described above. One or more such agents can be present in an anti-inflammatory effective total amount. Suitable anti-inflammatory agents include without limitation steroidal agents such as flucinolone and hydrocortisone, and nonsteroidal agents (NSAIDs) such as ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone and phenylbutazone. One or more anti-inflammatory agents are optionally present in the composition in an anti-inflammatory effective amount.

Compositions of the inventions optionally contain other ingredients such as enzymes, vitamins and anti-adhesion agents Enzymes such as proteases can be added for anti-stain and other effects. Non-limiting examples of vitamins include vitamin C, vitamin E, vitamin B5, and folic acid. In various embodiments, the vitamins have antioxidant properties. Anti-adhesion agents include ethyl lauroyl arginine (ELAH), solbrol, ficin, silicone polymers and derivatives, and quorum sensing inhibitors.

Among useful carriers for optional inclusion in a composition of the invention are diluents, abrasives, bicarbonate salts, pH modifying agents, surfactants, foam modulators, thickening agents, viscosity modifiers, humectants, sweeteners, flavorants and colorants. One carrier material, or more than one carrier material of the same or different classes, can optionally be present. Carriers should be selected for compatibility with each other and with other ingredients of the composition.

Water is a preferred diluent and in some compositions such as mouthwashes and whitening liquids is commonly accompanied by an alcohol, e.g., ethanol. The weight ratio of water to alcohol in a mouthwash composition is generally 1:1 to 20:1, for example 3:1 to 20:1 or 4:1 to 10:1. In a whitening liquid, the weight ratio of water to alcohol can be within or below the above ranges, for example 1:10 to 2:1.

In one embodiment a composition of the invention comprises at least one abrasive, useful for example as a polishing agent. Any orally acceptable abrasive can be used, but type, fineness (particle size) and amount of abrasive should be selected so that tooth enamel is not excessively abraded in normal use of the composition. Suitable abrasives include without limitation silica, for example in the foam of silica gel, hydrated silica or precipitated silica, alumina, insoluble phosphates, calcium carbonate, resinous abrasives such as urea-formaldehyde condensation products and the like. Among insoluble phosphates useful as abrasives are orthophosphates, polymetaphosphates and pyrophosphates. Illustrative examples are dicalcium orthophosphate dihydrate, calcium pyrophosphate, β-calcium pyrophosphate, tricalcium phosphate, calcium polymetaphosphate and insoluble sodium polymetaphosphate. One or more abrasives are optionally present in an abrasive effective total amount, typically 5% to 70%, for example 10% to 50% or 15% to 30% by weight of the composition. Average particle size of an abrasive, if present, is generally 0.1 to 30 μm, for example 1 to 20 μm or 5 to 15 μm. If silica is used as the abrasive, it is preferred that the amount of silica abrasive used be less than 6% by weight, more preferably, less than 4% silica abrasive, even more preferably less than 3% silica abrasive, and most preferably less than 2% silica abrasive.

In a further embodiment a composition of the invention comprises at least one bicarbonate salt, useful for example to impart a "clean feel" to teeth and gums due to effervescence and release of carbon dioxide. Any orally acceptable bicarbonate can be used, including without limitation alkali metal bicarbonates such as sodium and potassium bicarbonates, ammonium bicarbonate and the like. One or more bicarbonate salts are optionally present in a total amount of 0.1% to 50%, for example 1% to 20% by weight of the composition.

In a still further embodiment a composition of the invention comprises at least one pH modifying agent. Such agents include acidifying agents to lower pH, basifying agents to raise pH and buffering agents to control pH within a desired range. For example, one or more compounds selected from acidifying, basifying and buffering agents can be included to provide a pH of 2 to 10, or in various illustrative embodiments 2 to 8, 3 to 9, 4 to 8, 5 to 7, 6 to 10, 7 to 9, etc. Any orally acceptable pH modifying agent can be used, including without limitation carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and the like. One or more pH modifying agents are optionally present in a total amount effective to maintain the composition in an orally acceptable pH range.

In a still further embodiment a composition of the invention comprises at least one surfactant, useful for example to compatibilize other components of the composition and thereby provide enhanced stability, to help in cleaning the dental surface through detergency, and to provide foam upon agitation, e.g., during brushing with a dentifrice composition of the invention. Any orally acceptable surfactant, most of which are anionic, nonionic or amphoteric, can be used. Suitable anionic surfactants include without limitation water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium coconut monoglyceride sulfonate, sodium lauryl sarcosinate, sodium lauryl isoethionate, sodium laureth carboxylate and sodium dodecyl benzenesulfonate. Suitable nonionic surfactants include without limitation poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include without limitation derivatives of $C_{8-20}$ aliphatic secondary and tertiary amines having an anionic group such as carboxylate, sulfate, sulfonate, phosphate or phosphonate. A suitable example is cocoamidopropyl betaine. One or more surfactants are optionally present in a total amount of 0.01% to 10%, for example 0.05% to 5% or 0.1% to 2% by weight of the composition.

In a still further embodiment a composition of the invention comprises at least one foam modulator, useful for example to increase amount, thickness or stability of foam generated by the composition upon agitation. Any orally acceptable foam modulator can be used, including without limitation polyethylene glycols (PEGs), also known as polyoxyethylenes. High molecular weight PEGs are suitable, including those having an average molecular weight of 200,000 to 7,000,000, for example 500,000 to 5,000,000 or 1,000,000 to 2,500,000. One or more PEGs are optionally present in a total amount of 0.1% to 10%, for example 0.2% to 5% or 0.25% to 2% by weight of the composition.

In a still further embodiment a composition of the invention comprises at least one thickening agent, useful for example to impart a desired consistency and/or mouth feel to the composition. Any orally acceptable thickening agent can be used, including without limitation carbomers, also known as carboxyvinyl polymers, carrageenans, also known as Irish moss and more particularly l-carrageenan (iota-carrageenan), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, colloidal silica and the like. A preferred class of thickening or gelling agents includes a class of homopolymers of acrylic acid crosslinked with an alkyl ether of pentaerythritol or an alkyl ether of sucrose, or carbomers. Carbomers are commercially available from B.F. Goodrich as the Carbopol® series. Particularly preferred Carbopols include Carbopol 934, 940, 941, 956, 974P, and mixtures thereof. One or more thickening agents are optionally present in a total amount of 0.01% to 15%, for example 0.1% to 10% or 0.2% to 5% by weight of the composition.

In a still further embodiment a composition of the invention comprises at least one viscosity modifier, useful for example to inhibit settling or separation of ingredients or to promote redispersibility upon agitation of a liquid composition. Any orally acceptable viscosity modifier can be used, including without limitation mineral oil, petrolatum, clays and organomodified clays, silica and the like. One or more viscosity modifiers are optionally present in a total amount of 0.01% to 10%, for example 0.1% to 5% by weight of the composition.

In a still further embodiment a composition of the invention comprises at least one humectant, useful for example to prevent hardening of a tooth paste upon exposure to air. Any orally acceptable humectant can be used, including without limitation polyhydric alcohols such as glycerin, sorbitol, xylitol or low molecular weight PEGs. Most humectants also function as sweeteners. One or more humectants are optionally present in a total amount of 1% to 70%, for example 1% to 50%, 2% to 25%, or 5% to 15% by weight of the composition.

In a still further embodiment a composition of the invention comprises at least one sweetener, useful for example to enhance taste of the composition. Any orally acceptable natural or artificial sweetener can be used, including without limitation dextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, dipeptide-based intense sweeteners, cyclamates and the like. One or more sweeteners are optionally present in a total amount depending strongly on the particular sweetener(s) selected, but typically 0.005% to 5% by weight of the composition.

In a still further embodiment a composition of the invention comprises at least one flavorant, useful for example to enhance taste of the composition. Any orally acceptable natural or synthetic flavorant can be used, including without limitation vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants and the like. Also encompassed within flavorants herein are ingredients that provide fragrance and/or other sensory effect in the mouth, including cooling or warming effects. Such ingredients illustratively include menthol, menthyl acetate, menthyl lactate, camphor, eucalyptus oil, eucalyptol, anethole, eugenol, *cassia*, oxanone, α-irisone, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA) and the like. One or more flavorants are optionally present in a total amount of 0.01% to 5%, for example 0.1% to 2.5% by weight of the composition.

In a still further embodiment a composition of the invention may comprise at least one colorant in addition to the photosensitizing dye, although just the photosensitizing dye may be used to provide the color. Additional colorants may be employed to adjust the color, in the event the photosensitizing dye does not provide the appropriate aesthetically pleasing color. Colorants herein include pigments, dyes, lakes and agents imparting a particular luster or reflectivity such as pearling agents. A colorant can serve a number of functions, including for example to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including without limitation talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride and the like. One or more colorants are optionally present in a total amount of 0.001% to 20%, for example 0.01% to 10% or 0.1% to 5% by weight of the composition.

In various embodiments, the invention provides chewing gum compositions comprising a gum base and an effective amount of the combination of extracts discussed above. Chewing gum formulations typically contain, in addition, one or more plasticizing agents, at least one sweetening agent and at least one flavoring agent. The chewing gum formulations preferably are prepared using optically clear carriers to provide an optically clear chewing gum composition.

Gum base materials are well known in the art and include natural or synthetic gum bases or mixtures thereof. Representative natural gums or elastomers include chicle, natural rubber, jelutong, balata, guttapercha, lechi caspi, sorva, guttakay, crown gum, and perillo. Synthetic gums or elastomers include butadiene-styrene copolymers, polyisobutylene and isobutylene-isoprene copolymers. The gum base is incorporated in the chewing gum product at a concentration of 10 to 40% and preferably 20 to 35%.

In other embodiments, the oral compositions comprise an edible oral strip comprising one or more polymeric film forming agents and an effective amount of the combination of extracts discussed above. The one or more polymeric film forming agents are selected from the group consisting of orally acceptable polymers such as pullulan, cellulose derivatives, and other soluble polymers including those well-known in the art. Again, the polymer strip preferably is optically clear.

In various embodiments, the compositions are effective against a combination of oral bacteria, as shown for example, in artificial mouth antiplaque study. In various embodiments, significant reductions in plaque development are seen in comparison to a negative control containing none of the antibacterial composition.

The compositions of the invention show antibacterial activity as shown in a minimum inhibitory concentration (MIC) test on various oral microbes. The MIC test is well known in the art and its procedures need not be repeated here. The photosensitizing dyes useful in the compositions of the invention preferably have a MIC within the range of from 0.00001% to 10% weight/volume (w/v), preferably from 0.00005% to 5%, and even more preferably from 0.0001% to 1% w/v.

Photosensitizing dyes useful in the embodiments also have an anti-inflammatory effect. Pro-inflammation cytokines such as IL-6, IL-8, and TNFα can be decreased using the photosensitizing dyes described herein.

The preferred embodiments now will be described in more detail with reference to the following non-limiting examples.

SPECIFIC EMBODIMENTS OF THE INVENTION

Example 1

MIC is defined as the lowest concentration of an antimicrobial agent that will inhibit the growth of a microorganism and is usually expressed as ppm (μg/mL). MIC was determined by the Broth Dilution Method. To determine MIC, a series of culture tubes was prepared, each tube containing the growth medium (Broth) with a decreasing concentration of the antimicrobial agent. The tubes were then inoculated with the test organism and incubated at 37° C. After incubation, tubes were visually examined for growth as indicated by turbidity. The lowest concentration that prevented visible growth is the MIC. The MIC for the photosensitizing dyes described below typically ranged from 0.0001% (w/v) to 1% (w/v).

Bacterial biofilms (24 h old) were treated with the photosensitizers or photo-triggered actives described in the tables below at a concentration less than their minimum inhibitory concentration (MIC). The actives were either pre-incubated before light exposure for 2 s to 15 min, typically less than 2 min, or administered at the same time the biofilm was exposed to the light. The bacteria were irradiated at a set wavelength for 2 s to 15 min (typically less than 2 min) at an energy dose between 1-450 J/cm$^2$. Optical power densities typically ranged from 1-500 mW/cm$^2$. Light was either pulsed or provided in one continuous light exposure. Pulsed light treatments were preferred for high optical energy treatments.

In one embodiment, LED light alone is used to provide site-specific targeted oral care treatment where the light is focused to a particular region(s) in the oral cavity. In another embodiment, multiple wavelengths of light are used to provide multiple, oral care benefits such as the simultaneous and selective killing of black-pigmented bacteria with blue light (450±10 nm) while providing soft-tissue pain reduction and anti-inflammation with low-level red light.

Typical Oral Care Formulations for Use with Light

TABLE 3

Dentifrice Formulation

| Ingredient Name | Example 1 |
| --- | --- |
| Sodium CMC-7MF-Food Grade | 0.650 |
| Polyethylene Glycol 600 (PEG-12) | 3.000 |
| Sorbitol-Non-Browning/Non-crys NF-Sol | 56.438 |
| FC Brighter Flavor K91-5661 | 1.15 |
| Sodium Saccharin | 0.300 |
| Sodium Fluoride | 0.243 |
| Tetrasodium pyrophosphate | 0.500 |
| GRAS Dye | 0.400 |
| Zeodent 105-HCS | 20.000 |
| Zeodent 165-Synth-amorphous ppt silica | 4.25 |
| Cocamidopropyl betaine | 1.25 |
| Sodium lauryl sulfate | 1.50 |
| Demineralized water | 10.319 |
| Total Materials | 100 |

TABLE 4

Mouth Rinse Formulation

| Ingredient Name | Example 1 |
| --- | --- |
| Glycerin | 8 |
| 95% EtOH | 10 |
| PEG-40 Sorbitan Diisosterate-Animal Source | 0.15 |
| Dental Cream Flavor | 0.10 |
| Saccharin | 0.01 |
| Tartrazine | 0.1 |
| Purified water | 81.64 |
| Total Materials | 100 |

TABLE 5a

Rinse Delivered through a Toothbrush

| Ingredient Name | Example 1 |
| --- | --- |
| Glycerin | 8 |
| 95% EtOH | 10 |
| PEG-40 Sorbitan Diisosterate-Animal Source | 40 |
| Dental Cream Flavor | 30 |
| Saccharin | 2.5 |
| Tartrazine | 1.0 |
| Purified water | 8.5 |
| Total Materials | 100 |

TABLE 5b

Typical Target Oral Microbes:

| | |
| --- | --- |
| F. nucleatum | F. nuc. ss polymorph |
| P. gingivalis | C. gracilis |
| P. intermedia | T. forsythia |
| C. rectus | P. melaninogenica |
| A. actinomycetecomitans | F. periodonticum |
| A. naeslundii | P. denticola |
| L. casei | P. micros |
| S. gordonii | P. loeschii |
| S. mutans | F. nuc. ss vincentii |
| S. oralis | C. ochracea |
| S. sanguinis | |
| S. sobrinus | |

On a biofilm of *A. naeslundi*, the impact of four "photosensitizers" (0.1% concentration) in the presence of light was evaluated. MIC typically ranged from 0.0001% (w/v) to 1% (w/v). The percent biofilm reduction is tabulated below. Riboflavin, Allura Red tartrazine, Fast Green and Lissamine Green provide increased biofilm reduction compared to light alone.

TABLE 6

Percent Reduction in Biofilm

| | Percentage Reduction in Biofilm | |
| --- | --- | --- |
| Potential Photosensitizer | Light Alone | Light plus photosensitizer |
| Chlorophyllin sodium copper salt (405 nm) | 42% | 21% |
| Riboflavin (450 nm) | 28% | 56% |
| Allura Red (505 nm) | 23% | 55% |
| Indigo Carmine (608 nm) | 52% | 30% |
| Erioglaucine (405 nm) | 45% | 41% |
| Tartrazine (425 nm) | 52% | 72% |
| Chromotrope (525 nm) | 20% | 18% |
| Fast Green (625 nm) | 18% | 43% |
| Lissamine Green B (630 nm) | 14% | 43% |

Dosage for each wavelength: 24 J/cm$^2$ (200 mW/cm$^2$ @ 2 min). Each photosensitizer incubated for 2 min prior to irradiation.

The data in the table above reveals that light alone at the wavelengths, dosages and optical density, was effective in reducing biofilm, and consequently, would be effective in reducing bacteria and plaque formation in the oral cavity. The data also show that for many of the photosensitizing dyes, the presence of the dyes resulted in a dramatic increase in reduction of biofilm, compared with the use of just light alone.

Example 2

Cells used in this example include human embryonic palatal mesenchymal (HEFM) cells and oral keratinocytes OBA9 cells. The embodiments also can be used with other cells such as human gingival fibroblasts (HGF). Cells were seeded in 24-well plates and cultured until reaching a confluence above 80%. The confluent-stage cells were treated with stimulants such as IL-1β followed by light irradiation alone, or light irradiation combined with GRAS photosensitizing dye. The cells were either pre-incubated in photosensitizing dye before light exposure, or administered at the same time of light exposure. The cells were incubated in photosensitizing dyes for varied amounts of time, the concentration of photosensitizing dyes were varied, and the cell were irradiated with light for varied amounts of time per exposure, as well as irradiation either one time or multiple times, as described below. After irradiation, the cells were incubated at 37° C. The cell culture media was collected after a certain amount of time for cytokine analysis.

The results tabulated below reveal that visible light (various wavelength, 380-700 nm) alone and photosensitizing dye irradiated with visible light (various wavelength, 380-700 nm) have anti-inflammation effect. Results shown below reveal that light exposure at 625 nm for 2 minutes each time (dosage: 9 mW/cm$^2$, 1.1 J/cm$^2$), single exposure or multiple exposure, can decrease pro-inflammation cytokines IL-6 and IL-8 concentration in the in vitro cell culture. The results further show that photosensitizing dye Fast Green at 1000 ppm combined with light exposure at 625 nm for 2 minutes (dosage: 9 mW/cm$^2$, 1.1 J/cm$^2$) can decrease pro-inflammation cytokine TNFα concentration in the in vitro cell culture. The results are shown in the tables below

TABLE 7

| Cytokine Conc. (pg/ml) | Stimulant | | | | | |
|---|---|---|---|---|---|---|
| | Control | Il-1β | Il-1β + light (1) | Il-1β + light (2) | Il-1β + light (3) | Il-1β + light + Dye |
| Il-6 | 0 | 1400 | 980 | 630 | 580 | |
| IL-8 | 0 | 4500 | 1900 | 1,100 | 1,600 | |
| TNF-α | 0 | 9 | 5.8 | | | 3.4 |

The Control in Table 7 was no stimulation, and hence, no inflammation and production of cytokine. Stimulation with 11-1β was to simulate inflammation in the cells, and consequent production of 11-6, 11-8 and TNF-α. As shown in Table 7 above, light at 625 nm can reduce concentration of IL-6 of oral keratinocyte OBA9 cells stimulated by IL-1β. Each light exposure was 2 minutes, dosage: 9 mW/cm$^2$, 1.1 J/cm$^2$. Table 7 also shows that light at 625 nm can reduce concentration of IL-8 of oral keratinocyte OBA9 cells stimulated by IL-1β. Each light exposure was 2 minutes, dosage: 9 mW/cm$^2$, 1.1 J/cm$^2$. Finally, light at 625 nm alone and light combined with Fast Green at 1000 ppm can reduce concentration of TNFα of HEPM cells stimulated by IL-1β. Light exposure was 2 minutes, dosage: 9 mW/cm$^2$, 1.1 J/cm$^2$.

Example 3

This example includes a series of experiments to assess the transmission of LED light at certain wavelengths through toothpaste pastes and toothpaste gels. The following compositions were tested:

TABLE 8

| Base Dentifrice Formulation with 15% Hole | |
|---|---|
| Ingredient Name | Formula AI (%) |
| PEG 600 (PEG-12) NF | 3 |
| Sorbitol | 70 |
| Na CMC | 0.6 |
| COP Carbopol 974P | 0.9 |
| Silica Hole | 0 |
| GRAS Dye or Photosensitizer | 0 |
| Hole | 15 |
| Na Benzoate | 0.5 |
| Water | 10 |

The base dentifrice was prepared as follows. PEG, Sorbitol, Na CMC, COP Carbopol, Water, and Na Benzoate were added and mixed together in that order. Adding the PEG and the sorbitol first allows for the CMC and the carbopol to disperse in solution. After allowing the polymers to disperse, water was added before Na Benzoate to facilitate the preservative to disperse into solution faster. The optical clarity of the above base composition visually matched that of the humectant (sorbitol+water) and the composition containing 3-8% abrasive or silica. However, 3% silica provided the most optically clear version of the formula.

The combination of CMC and carbopol provided what appeared to be the superior consumer consistency with respect to typical dentifrice viscosities. CMC/Carbopol/benzoate 0.5% also provided favorable micro-robustness. The 15% hole can be used to accommodate different ingredients such as humectants, odor-masking ingredients, anti-inflammatory actives, stabilizers, binders, humectants, sweetners, flavors, surfactants, fluoride, arginine bicarbonate, abrasives, optical fluids, strips, beads, foam inducing agents etc.

TABLE 9

| Dentifrice Formulation with a GRAS dye Tartrazine | |
|---|---|
| Ingredient Name | Formula AI (%) |
| Base formulation (see Table 7) | 85 |
| Silica | 3 |
| Tartrazine | 0.01 |
| Water | 11 |

The GRAS dye tartrazine can be formulated between 0.001% and 1% though typically, 0.01%. Other GRAS dyes that can be used include Allura Red, Fast Green, and Curcumin. In Table 15 below, the Allura Red and Fast Green formulations were identical to the formulation above, except the tartrazine was replaced with either Allura Red or Fast Green.

TABLE 10

| Dentifrice with No TiO$_2$ | |
|---|---|
| Ingredient Name | Formula AI (%) |
| Base | 85 |
| Silica | 3 |
| Tartrazine | 0.01 |
| SLS | 1.17 |
| Flavor | 1 |
| TiO$_2$ | 0 |
| Water | 8.799 |

This formulation contained additional toothpaste ingredients (sodium lauryl sulfate (SLS) and flavor), and retained its optical transparency, but when titanium oxide was included the dentifrice became opaque. Toothpastes with little or no titanium oxide would need less optical dosage for anti-bacterial efficacy. Accordingly, it is preferred in the embodiments to use oral care compositions that are optically clear. A Dentifrice with $TiO_2$ was prepared as shown in Table 10 below.

TABLE 11

Dentifrice with $TiO_2$

| Ingredient Name | Formula AI (%) |
|---|---|
| Base | 85 |
| Silica | 3 |
| Tartrazine | 0.01 |
| SLS | 1.17 |
| Flavor | 1 |
| $TiO_2$ | 0.3 |
| Water | 8.499 |

Other toothpaste formulations were prepared as shown in the tables below.

TABLE 12

Cavity Protection

| Ingredient Name | Formula AI (%) |
|---|---|
| Cavity Protection Toothpaste | 99.98 |
| Tartrazine | 0.01 |
| Water | 0.01 |

A similar toothpaste was prepared, but no photosensitizing dye was added.

TABLE 13

Tartar Control

| Ingredient Name | Formula AI (%) |
|---|---|
| Tartar Protection Toothpaste | 99.98 |
| Tartrazine | 0.01 |
| Water | 0.01 |

A similar toothpaste was prepared, but no photosensitizing dye was added.

TABLE 14

Dentifrice Formulation with 0.01% Curcumin

| Ingredient Name | Formula AI (%) |
|---|---|
| PEG 600 (PEG-12) NF | 3 |
| Sorbitol | 70 |
| Na CMC | 0.6 |
| Carbopol 974P | 0.9 |
| Silica | 3 |
| Curcumin Dye | 0.01 |
| Hole | 0 |
| Na Benzoate | 0.5 |
| Water | 21 |

The impact of the different dentifrice and their slurries on light transmission at 425 nm was provided as an example. If a dentifrice or its slurry reduces the optical density of the LED emanating through a clear plastic covering, then that dentifrice or slurry has a negative impact on light transmission. The following experiments were carried out to determine the effect of different dentifrice formulations had on optical clarity, or light transmission.

LEDs transmitting light at 425 nm were covered with a clear plastic cover, and then a liner was placed on top of the cover. The liner served to ensure that light density was measured at an equal distance from the sample for all samples. The light density was measured to determine the light density of the LEDs without any oral composition (paste or slurry or gel). This light density was an initial reading to which other readings were compared.

The impact of various pastes on light transmission of the LED was determined first by placing a sample of paste or gel across the clear cover, and then using a casting bar to equilibrate the depth of the paste or gel to the depth of the clear cover. The light density then was measured of the paste or gel in the same manner as described above, and the difference between the two was used to calculate the percent reduction of light transmission.

The method used to asses the percent reduction of light transmission for slurries was carried out by first covering the LEDs with a clear cover and then placing a microscope slide on tope of the clear cover, directly above the LEDs. The light density was measured as described above to obtain an initial reading to which other readings were compared. Then, 1000 of slurry having a 1:2 (paste or gel) to water weight ratio, were added to each well on top of the clear cover, and microscope slide was then placed on top of the slurry. The light density was again measured, and the difference between the two was used to calculate the percent reduction of light transmission (or increase in light transmission, as the case may be).

The following samples were tested:

TABLE 15

| Sample | Description |
|---|---|
| Initial | Light Density of LED without Paste |
| I | Base formula without dye (Base Formula - Table 8) |
| A | Base formula control with 0.01% Tartrazine (Table 9) |
| B | Base formula control with 0.1% Tartrazine (modified Table 9) |
| E | Additional TP ingredients (no TiO2)-only SLS and flavor (Table 10) |
| F | Additional TP ingredients (w/ TiO2) (Table 11) |
| J | Base formula with 0.01% Curcumin (Table 14) |
| C | Fast Green formula (Table 9 with Fast Green instead of Tartrazine) |
| D | Allura Red formula (Table 9 with Allura Red instead of Tartrazine) |
| K | Cavity Protection w/o dye (Table 12) |
| G | Cavity Protection w/ 0.01% Tartrazine (Table 12 with Tartrazine) |
| L | Tartar Control TP w/o dye (Table 13) |
| H | Tartar Control TP w/ 0.01% Tartrazine (Table 13 with Tartrazine) |

Ribbons of each dentifrice were placed on clear paper marked with crosses to provide a quick assessment of the degree of light transmission through them. Samples I (clear-white), A (yellow), and B (yellow) provided gels in which the crosses could be clearly seen. The crosses could be seen in Sample E (yellow), although not as clearly as samples I, A, and B. Samples F (yellow), K (white), G (yellow), L (white), and H (yellow) all provided gels in which the crosses could not be seen. The crosses also could clearly be seen through samples J (yellow), C (blue-green), and D (red).

The samples A-L were all tested for reduction in light transmission either as the paste, or as a slurry (1:2 weight ratio of paste to water). The results are presented in the following Table.

TABLE 16

Light Transmission

| Sample | Percent Reduction in Light Transmission | |
| --- | --- | --- |
| | Paste | Slurry |
| I | 2% increase | 5% |
| A | 37% | 7% |
| B | 95% | 60% |
| E | 22% | 10% |
| F | 96% | 48% |
| J | 2% | 5% |
| C | 6% | 5% increase |
| D | 2% | 2% increase |
| K | 83% | |
| G | 94% | 75% |
| L | 82% | |
| H | 97% | 68% |

The results from Table 16 reveal that the light density of the LED without paste and the intensity of the light when viewed through the toothpaste without a GRAS dye are virtually identical. That is, the dentifrice with the GRAS dye has been designed and formulated to have little or no negative impact on light transmission versus the formulation with no dye. The light density was reduced when 0.01% tartrazine was added to the base toothpaste formulation, and even further reduced when the dye level is increased to 0.1% (compare reduction in transmission between samples A and B). The light density at 425 nm remains nearly the same when green or red dyes are used instead of the yellow GRAS dye.

It also can be seen from Table 16 that the addition of SLS and flavor to the base formulation slightly increased light density (compare samples E and I). The addition of $TiO_2$ to the Carbopol based foimulation drastically decreases light density and transmission. Current Colgate® products on the market (samples G (Cavity protection) and H (tartar control)) obtained a light density similarly to the light formulation with $TiO_2$ (sample F).

To improve light transmission and provide an optically clear oral care composition, the compositions should preferably contain little or no $TiO_2$, contain a photosensitizing dy such as tartrazine, curcumin, Fast Green, Allura Red, and the like, and contain 3% silica or less as the abrasive.

The invention has been described above with reference to illustrative Examples, but it is to be understood that the invention is not limited to the disclosed embodiments. Alterations and modifications that would occur to one of skill in the art upon reading the specification are also within the scope of the invention, which is defined in the appended claims.

We claim:

1. A kit for treating and/or preventing conditions caused by microorganisms in a subject, the kit comprising an optically clear oral care composition comprising a photosensitizing dye, and a light emitting device capable of emitting light at a wavelength and for a period of time sufficient to activate the photosensitizing dye to treat and/or prevent the condition caused by microorganisms, wherein the photosensitizing dye is selected from the group consisting of
Tartrazine (FD&C Yellow No. 5),
Riboflavin 5'-monophosphate sodium salt,
Allura Red AC (FD&C Red No. 40),
Fast Green FCF (FD&C Green No. 3),
Lissamine Green B,
and mixtures thereof;
the optically clear oral care composition further comprising perfluorodecahydro naphthalene, and
the composition being free of titanium dioxide and containing 1-3% silica.

2. The kit as claimed in claim 1, further comprising an applicator that is capable of applying the oral care composition to the oral cavity.

3. The kit as claimed in claim 1, wherein the applicator also is the light emitting device, and is capable of irradiating the area to which the composition is administered with the applicator.

4. The kit as claimed in claim 1, wherein the light emitting device is capable of emitting light at a wavelength from 380 nm to 780 nm, at a dosage of from 1 $J/cm^2$ to 450 $J/cm^2$, with a power density of from about 1 to about 500 $mW/cm^2$, and for a period of time of from 1 second to 120 minutes.

5. The kit of claim 1, wherein the light has a wavelength of from 400 to 780 nm.

6. The kit of claim 1, wherein the period of time is from 2 seconds to 15 minutes.

7. The kit of claim 1, wherein light is emitted at a dosage of from 15 to 45 $J/cm^2$.

8. The kit of claim 1, wherein the light is emitted at a power density of from 175 to 250 $mW/cm^2$.

9. The kit of claim 1, wherein the photosensitizing dye is selected from the group consisting of Tartrazine, Allura Red, Fast Green FCF, and mixtures thereof.

10. The kit of claim 1, wherein the photosensitizing dye is present in an amount ranging from about 0.001 to about 1% by weight.

11. The kit of claim 1, wherein the composition is in a form selected from the group consisting of: a liquid solution suitable for irrigating, rinsing or spraying; a dentifrice selected from a powder, toothpaste or dental gel; a periodontal gel; a liquid suitable for painting a dental surface; a chewing gum; a dissolvable, partially dissolvable or non-dissolvable film or strip; a bead; a wafer; a lozenge; a wipe or towelette; an implant; a mouthrinse; a foam; and a dental floss.

12. The kit of claim 1, wherein the composition is a toothpaste, mouthrinse, or dental gel.

13. The kit of claim 1, further comprising instructions for applying the oral care composition and irradiating the oral cavity with the light emitting device.

14. A kit for treating and/or preventing conditions caused by microorganisms in a subject, comprising:
a) an optically clear toothpaste which is free of titanium dioxide containing:
i) a photosensitizing dye selected from the group consisting of
Tartrazine (FD&C Yellow No. 5),
Riboflavin 5'-monophosphate sodium salt,
Allura Red AC (FD&C Red No. 40),
Fast Green FCF (FD&C Green No. 3),
Lissamine Green B,
and mixtures thereof;
ii) 1-3% silica; and
iii) perfluorodecahydro naphthalene; and
b) a light emitting device capable of emitting light at a wavelength and for a period of time sufficient to activate the photosensitizing dye to treat and/or prevent the condition caused by microorganisms.

15. The kit of claim 14, wherein the light emitting device is capable of emitting light at a wavelength from 380 nm to 780 nm, at a dosage of from 1 $J/cm^2$ to 450 $J/cm^2$, with a power density of from about 1 to about 500 $mW/cm^2$, and for a period of time of from 1 second to 120 minutes.

16. The kit of claim 14, wherein the photosensitizing dye is tartrazine.

17. The kit of claim 14, wherein the photosensitizing dye is present in an amount ranging from about 0.001 to about 1% by weight.

18. The kit of claim 1, wherein the composition has total luminance transmission value of from 80 to 100.

19. The kit of claim 18, wherein the composition has total luminance transmission value of from 88 to 95.

20. The kit of claim 1, wherein the haze of the composition is <3.5%.

21. The kit of claim 1, wherein the haze of the composition is <2.5%.

* * * * *